United States Patent
Jung et al.

(10) Patent No.: US 9,890,129 B2
(45) Date of Patent: Feb. 13, 2018

(54) AMINOALKYLBENZOTHIAZEPINE DERIVATIVES AND USES THEREOF

(71) Applicant: CJ Healthcare Corporation, Seoul (KR)

(72) Inventors: Won-Hyuk Jung, Yongin-si (KR); Seung In Kim, Daejeon (KR); Seung Hee Ji, Seoul (KR); Dong Hyun Ko, Gwacheon-si (KR); Seog Beom Song, Suwon-si (KR); Keun Ho Lee, Seoul (KR); Hyung Jin Jun, Yongin-si (KR); Dong Kyu Kim, Yongin-si (KR); Dong Hyun Kim, Seongnam-si (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 15/506,634

(22) PCT Filed: Aug. 28, 2015

(86) PCT No.: PCT/KR2015/009044
§ 371 (c)(1),
(2) Date: Feb. 24, 2017

(87) PCT Pub. No.: WO2016/064082
PCT Pub. Date: Apr. 28, 2016

(65) Prior Publication Data
US 2017/0283386 A1    Oct. 5, 2017

(30) Foreign Application Priority Data

Oct. 20, 2014   (KR) .......... 10-2014-0141869
May 19, 2015    (KR) .......... 10-2015-0069949

(51) Int. Cl.
| | | |
|---|---|---|
| *A61P 1/00* | (2006.01) |
| *C07D 281/10* | (2006.01) |
| *C07D 281/08* | (2006.01) |
| *A61K 31/554* | (2006.01) |
| *C07C 13/24* | (2006.01) |
| *C07C 13/32* | (2006.01) |
| *C07C 317/06* | (2006.01) |

(52) U.S. Cl.
CPC .......... *C07D 281/10* (2013.01); *A61K 31/554* (2013.01); *C07C 13/24* (2013.01); *C07C 13/32* (2013.01); *C07C 317/06* (2013.01); *A61K 2300/00* (2013.01)

(58) Field of Classification Search
CPC ............... C07D 281/10; A61K 31/554; A61K 2300/00; C07C 13/24; C07C 13/32; C07C 317/06
USPC .......................................... 549/10
See application file for complete search history.

(56) References Cited

U.S. PATENT DOCUMENTS

| | | |
|---|---|---|
| 2004/0254160 A1 | 12/2004 | Starke et al. |
| 2006/0083790 A1 | 4/2006 | Anderberg |
| 2006/0094884 A1 | 5/2006 | Starke et al. |
| 2013/0029930 A1 | 1/2013 | Aquino et al. |
| 2013/0338093 A1 | 12/2013 | Gedulin et al. |

OTHER PUBLICATIONS

"Elobixibat for the treatment of constipation" Wong; Expert Opin. Investig. Drugs 2013, 22, 277-284. (Year: 2013).*
"Discovery of a Highly Potent, Nonabsorbable Apical Sodium-Dependent Bile Acid Transporter Inhibitor (GSK2330672) for Treatment of Type 2 Diabetes" Wu; J. Med. Chem. 2013, 56, 5094-5114. (Year: 2013).*
Banny S. Wong, et al., "Effects of A3309, an Ileal Bile Acid Transporter Inhibitor, on Colonic Transit and Symptoms in Females with Functional Constipation", American Journal of Gastroenterology, 2011, 106, pp. 2154-2163.
International Search Report in connection with PCT International Application No. PCT/KR2015/009044, dated Mar. 2016.

* cited by examiner

*Primary Examiner* — Daniel R Carcanague
(74) *Attorney, Agent, or Firm* — John P. White; Cooper & Dunham LLP

(57) ABSTRACT

The present invention relates to a novel aminoalkylbenzothiazepine derivative or a pharmaceutically acceptable salt thereof, and a pharmaceutical composition for preventing or treating constipation comprising the same as an active ingredient.

14 Claims, No Drawings

AMINOALKYLBENZOTHIAZEPINE DERIVATIVES AND USES THEREOF

CROSS-REFERENCE TO RELATED APPLICATIONS

This application is a §371 national stage of PCT International Application No. PCT/KR2015/009044, filed Aug. 28, 2015, claiming priority of Korean Patent Applications Nos. KR 10-2015-0069949, filed May 19, 2015 and KR 10-2014-0141869, filed Oct. 20, 2014, the content of each of which is hereby incorporated by reference into the application.

TECHNICAL FIELD

The present invention relates to a novel aminoalkylbenzothiazepine derivative or a pharmaceutically acceptable salt thereof, and a pharmaceutical composition for preventing or treating constipation comprising the same as an active ingredient.

BACKGROUND ART

Constipation is a common digestive disease having a prevalence rate of about 16% in Korea. It occurs more frequently in women than in men, and the prevalence rate is higher in aged people, being about 30% to 40%. Due to the discomfort and serious effects on daily life, constipation has been surveyed as the second most important reason associated with absence for workers in western countries, and some constipation patients have been reported to experience a serious deterioration in their quality of life.

At present, stimulant laxatives and stool softeners are widely used for the treatment of constipation. Stimulant laxatives prevent the water absorption in the large intestine and stimulate the movement of the large intestine, and Senna™ and Bisacodyl™ are widely used. Additionally, stool softeners increase the water absorption by the feces by lowering the surface tension of the feces, and a representative example is Docusate™. However, these stimulant laxatives and stool softeners can only provide temporary effects and may develop resistance, and are thus not recommended for long-term use.

Meanwhile, bile acid is produced from cholesterol in the liver, stored in the gallbladder, and excreted into the small intestine to aid the digestion of nutrients such as lipids and vitamins after meals. About 90% of bile acid is resorbed to the liver while being transported into the lower part of the small intestine. The inhibition of bile acid resorption by a drug makes the bile acid move to the large intestine, and induces promotion of the water secretion within the large intestine and bowel movement therein, and is thus useful for the prevention and treatment of constipation (American Journal of Gastroenterology, 2011, 106: 2154-2163).

DISCLOSURE

Technical Problem

The present inventors, while endeavoring to develop a novel compound to be used for the prevention and treatment of constipation, discovered that a series of aminoalkylbenzothiazepine derivatives can effectively inhibit the resorption of bile acid, and are thus useful for the prevention and treatment of constipation, thereby completing the present invention.

Technical Solution

In an aspect, the present invention provides a compound represented by Formula 1 below, or a pharmaceutically acceptable salt thereof:

[Formula 1]

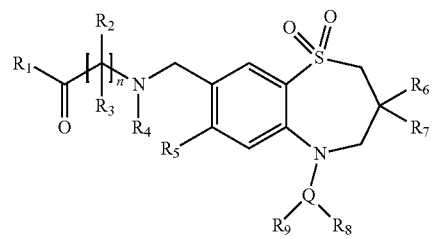

wherein
$R_1$ is hydroxy, carboxy, or hydroxysulfonyl($C_{1-4}$ alkyl);
$R_2$ and $R_3$ are each independently hydrogen, $C_{1-4}$ alkyl, hydroxy ($C_{1-4}$ alkyl), carbamoyl($C_{1-4}$ alkyl), carboxy, carboxy($C_{1-4}$ alkyl), ($C_{5-10}$ heteroaryl)($C_{1-4}$ alkyl), or ($C_{5-10}$ aryl)($C_{1-4}$ alkyl), or $R_2$ and $R_3$, taken together with the respective carbon atom to which they are attached, form $C_{3-7}$ cycloalkylene;
$R_4$ is hydrogen or carboxy($C_{1-4}$ alkyl);
$R_5$ is hydrogen, halogen, ($C_{1-4}$ alkyl)thio, ($C_{1-4}$ alkyl)amino, or di($C_{1-4}$ alkyl)amino;
$R_6$ and $R_7$ are each independently $C_{1-6}$ alkyl;
$R_8$ and $R_9$ are each independently hydrogen, hydroxy, $C_{1-4}$ alkoxy, $C_{1-4}$ alkyl, halogen, nitro, cyano, amino, ($C_{1-4}$ alkyl)amino, di($C_{1-4}$ alkyl)amino, acetamido, formyl, $C_{1-4}$ alkanoyl, carboxy, carbamoyl, ($C_{1-4}$ alkyl)carbamoyl, di($C_{1-4}$ alkyl)carbamoyl, carbamoyloxy, ($C_{1-4}$ alkyl)carbamoyloxy, di($C_{1-4}$ alkyl)carbamoyloxy, ($C_{1-4}$ alkyl)sulfonyloxy, sulfamoyloxy, ($C_{1-4}$ alkyl)sulfamoyloxy, or di($C_{1-4}$ alkyl)sulfamoyloxy;
Q is $C_{5-10}$ aryl or $C_{5-10}$ heteroaryl; and
n is an integer of 0 to 3.
Preferably, in Formula 1 above,
$R_1$ is hydroxy, carboxy, or hydroxysulfonyl($C_{1-4}$ alkyl);
$R_2$ and $R_3$ are each independently hydrogen, $C_{1-4}$ alkyl, hydroxy($C_{1-4}$ alkyl), carbamoyl($C_{1-4}$ alkyl), carboxy, carboxy($C_{1-4}$ alkyl), or ($C_{5-10}$ heteroaryl)($C_{1-4}$ alkyl), or $R_2$ and $R_3$, taken together with the respective carbon atom to which they are attached, form $C_{3-7}$ cycloalkylene;
$R_4$ is hydrogen or carboxy($C_{1-4}$ alkyl);
$R_5$ is ($C_{1-4}$ alkyl)thio;
$R_6$ and $R_7$ are each independently $C_{1-6}$ alkyl;
$R_8$ and $R_9$ are each independently hydrogen, hydroxy, halogen, or $C_{1-4}$ alkoxy;
Q is $C_{5-10}$ aryl; and
n is an integer of 0 to 3.
Preferably, in Formula 1 above, $R_1$ may be hydroxy, carboxy, or hydroxysulfonylmethyl.
Preferably, in Formula 1 above, $R_2$ and $R_3$ may each independently be hydrogen, carboxy, methyl, isobutyl, carbamoylmethyl, carboxymethyl, carboxyethyl, hydroxymethyl, imidazolylmethyl, indolylmethyl, or ethyl, or $R_2$ and $R_3$ taken together with the respective carbon atom to which they are attached, may form cyclopropylene.
Preferably, in Formula 1 above, $R_4$ may be hydrogen, carboxymethyl, or carboxyethyl.
Preferably, in Formula 1 above, $R_5$ may be methylthio, ethylthio, or dimethylamino.

Preferably, in Formula 1 above, $R_6$ and $R_7$ may be both butyl or both ethyl.

Preferably, in Formula 1 above, $R_8$ and $R_9$ may each independently be hydrogen, hydroxy, methoxy, methyl, ethyl, fluoro, chloro, nitro, cyano, amino, methylamino, ethylamino, dimethylamino, acetyl, carboxy, carbamoyl, methylcarbamoyl, dimethylcarbamoyl, carbamoyloxy, methylcarbamoyloxy, dimethylcarbamoyloxy, methylsulfonyloxy, sulfamoyloxy, methylsulfamoyloxy, or dimethylsulfamoyloxy.

Preferably, in Formula 1 above, Q may be phenyl, pyridinyl, pyrimidinyl, or thiophenyl. According to Formula 1 above, Q may be phenyl, pyridinyl, pyrimidinyl, or thiophenyl, which are substituted with $R_8$ and $R_9$. In Q' above, the positions of substituents, $R_8$ and $R_9$, are not determined but they may be located on mutually different atoms, and hydrogen may be bound to positions other than these positions. Accordingly, when both $R_8$ and $R_9$ are hydrogen, Q may refer to phenyl, pyridinyl, pyrimidinyl, or thiophenyl, which are not substituted.

More preferably, the compound may be:

1) 2-(((3,3-dibutyl-7-methylthio-1,1-dioxido-5-phenyl-2,3,4,5-tetrahydrobenzo[b][1,4]thiazepine-8-yl)methyl)amino)acetic acid;
2) 3-(((3,3-dibutyl-7-methylthio-1,1-dioxido-5-phenyl-2,3,4,5-tetrahydrobenzo[b][1,4]thiazepine-8-yl)methyl)amino)propanoic acid;
3) 2-(((3,3-dibutyl-7-methylthio-1,1-dioxido-5-phenyl-2,3,4,5-tetrahydrobenzo[b][1,4]thiazepine-8-yl)methyl)amino)succinic acid;
4) (S)-2-(((3,3-dibutyl-7-methylthio-1,1-dioxido-5-phenyl-2,3,4,5-tetrahydrobenzo[b][1,4]thiazepine-8-yl)methyl)amino)propanoic acid;
5) 2-(((3,3-dibutyl-7-methylthio-1,1-dioxido-5-phenyl-2,3,4,5-tetrahydrobenzo[b][1,4]thiazepine-8-yl)methyl)amino)pentanedioic acid;
6) 4-amino-2-(((3,3-dibutyl-7-methylthio-1,1-dioxido-5-phenyl-2,3,4,5-tetrahydrobenzo[b][1,4]thiazepine-8-yl)methyl)amino)-4-oxobutanoic acid;
7) (R)-2-(((3,3-dibutyl-7-methylthio-1,1-dioxido-5-phenyl-2,3,4,5-tetrahydrobenzo[b][1,4]thiazepine-8-yl)methyl)amino)propanoic acid;
8) 2-(((3,3-dibutyl-7-methylthio-1,1-dioxido-5-phenyl-2,3,4,5-tetrahydrobenzo[b][1,4]thiazepine-8-yl)methyl)amino)-2-methylpropanoic acid;
9) (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-imidazol-4-yl)propanoic acid;
10) (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-indol-2-yl)propanoic acid;
11) (S)-2-(((3,3-dibutyl-7-methylthio-1,1-dioxido-5-phenyl-2,3,4,5-tetrahydrobenzo[b][1,4]thiazepine-8-yl)methyl)amino)-4-methylpentanoic acid;
12) (S)-2-(((3,3-dibutyl-7-methylthio-1,1-dioxido-5-phenyl-2,3,4,5-tetrahydrobenzo[b][1,4]thiazepine-8-yl)methyl)amino)pentanedioic acid;
13) (S)-2-(((3,3-dibutyl-7-methylthio-1,1-dioxido-5-phenyl-2,3,4,5-tetrahydrobenzo[b][1,4]thiazepine-8-yl)methyl)amino)-3-hydroxypropanoic acid;
14) 3-((carboxymethyl)((3,3-dibutyl-7-methylthio-1,1-dioxido-5-phenyl-2,3,4,5-tetrahydrobenzo[b][1,4]thiazepine-8-yl)methyl)amino)propanoic acid;
15) 3-(((3,3-dibutyl-7-methylthio-1,1-dioxido-5-phenyl-2,3,4,5-tetrahydrobenzo[b][1,4]thiazepine-8-yl)methyl)amino)pentanedioic acid;
16) 2-(((3,3-dibutyl-7-methylthio-1,1-dioxido-5-phenyl-2,3,4,5-tetrahydrobenzo[b][1,4]thiazepine-8-yl)methyl)amino)-2-oxoacetic acid;
17) 1-(((3,3-dibutyl-7-methylthio-1,1-dioxido-5-phenyl-2,3,4,5-tetrahydrobenzo[b][1,4]thiazepine-8-yl)methyl)amino)cyclopropanecarboxylic acid;
18) 2-(((3,3-dibutyl-7-methylthio-1,1-dioxido-5-phenyl-2,3,4,5-tetrahydrobenzo[b][1,4]thiazepine-8-yl)methyl)amino)-2-oxoethanesulfonic acid;
19) 2-(((3,3-dibutyl-5-(4-methoxyphenyl)-7-methylthio-1,1-dioxido-2,3,4,5-tetrahydrobenzo[b][1,4]thiazepine-8-yl)methyl)amino)acetic acid;
20) 2-(((3,3-dibutyl-5-(4-hydroxyphenyl)-7-methylthio-1,1-dioxido-2,3,4,5-tetrahydrobenzo[b][1,4]thiazepine-8-yl)methyl)amino)acetic acid;
21) 2-(((3,3-dibutyl-5-(3-methoxyphenyl)-7-methylthio-1,1-dioxido-2,3,4,5-tetrahydrobenzo[b][1,4]thiazepine-8-yl)methyl)amino)acetic acid;
22) 2-(((3,3-dibutyl-5-(4-fluorophenyl)-7-methylthio-1,1-dioxido-2,3,4,5-tetrahydrobenzo[b][1,4]thiazepine-8-yl)methyl)amino)acetic acid;
23) 2-(((3,3-dibutyl-5-(3-fluorophenyl)-7-methylthio-1,1-dioxido-2,3,4,5-tetrahydrobenzo[b][1,4]thiazepine-8-yl)methyl)amino)acetic acid;
24) 2-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)acetic acid;
25) 2-(((3,3-dibutyl-5-(4-methoxyphenyl)-7-methylthio-1,1-dioxido-2,3,4,5-tetrahydrobenzo[b][1,4]thiazepine-8-yl)methyl)amino)-2-oxoethanesulfonic acid;
26) 1-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)cyclopropanecarboxylic acid;
27) 2-(((3,3-dibutyl-5-(4-fluorophenyl)-7-methylthio-1,1-dioxido-2,3,4,5-tetrahydrobenzo[b][1,4]thiazepine-8-yl)methyl)amino)-2-oxoacetic acid;
28) (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)propanoic acid;
29) (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)-3-hydroxypropanoic acid; and
30) 1-(((3,3-dibutyl-5-(4-fluorophenyl)-7-methylthio-1,1-dioxido-2,3,4,5-tetrahydrobenzo[b][1,4]thiazepine-8-yl)methyl)amino)cyclopropanecarboxylic acid.

Additionally, the compound of the present invention may be present in the form of a pharmaceutically acceptable salt. For the salt, acid addition salts formed by pharmaceutically acceptable free acids may be useful. As used herein, the term "pharmaceutically acceptable salt" refers to any organic or inorganic addition salt of the above compounds, which has a concentration for exhibiting an effective action, being relatively non-toxic and unharmful to patients, and the adverse effects resulting from the salt do not deteriorate the advantageous effects of the compounds represented by Formula 1.

Acid addition salts may be prepared by a conventional method, for example, by dissolving the compounds in an excess amount of aqueous acid solution, followed by precipitating the salt in a water-miscible organic solvent, e.g., methanol, ethanol, acetone, or acetonitrile. An equimolar amount of a compound and the acid or alcohol (e.g., glycol monomethyl ether) in water is heated and then the mixture is dried by evaporation, or the precipitated salt may be subjected to suction filtration.

Additionally, a pharmaceutically acceptable metal salt may be prepared using a base. Alkali metal salts or alkali earth metal salts may be prepared, for example, by dissolving the compound in an excess amount of alkali metal hydroxide or alkali earth metal hydroxide solution, filtering non-dissolving compound salts, evaporating and drying the filtrate.

The pharmaceutically acceptable salt of the present invention, unless otherwise indicated, may include a salt of the acidic or basic group that can be present in the compound of Formula 1, and may be prepared by a method of preparing salts known in the art.

Furthermore, the compounds of the present invention have an asymmetric carbon center in the parent structure and the substituent group thereof, and thus they can be present as R or S isomers, racemates, stereoisomer mixtures, and individual stereoisomers, and all these isomers and mixtures thereof belong to the scope of the present invention.

For instance, the compounds of the present invention may be synthesized from amino-alkoxybenzenethiol and 3-bromo-2-(mono or di)alkylpropanoic acid by a series of reactions shown in Reaction Scheme 1 below. However, the Reaction Scheme shown below is only a method for illustrative purposes, but the method of preparing the compounds of the present invention is not limited thereto, and any method known in the art may be used or adjusted appropriately for use.

[Reaction Scheme 1]

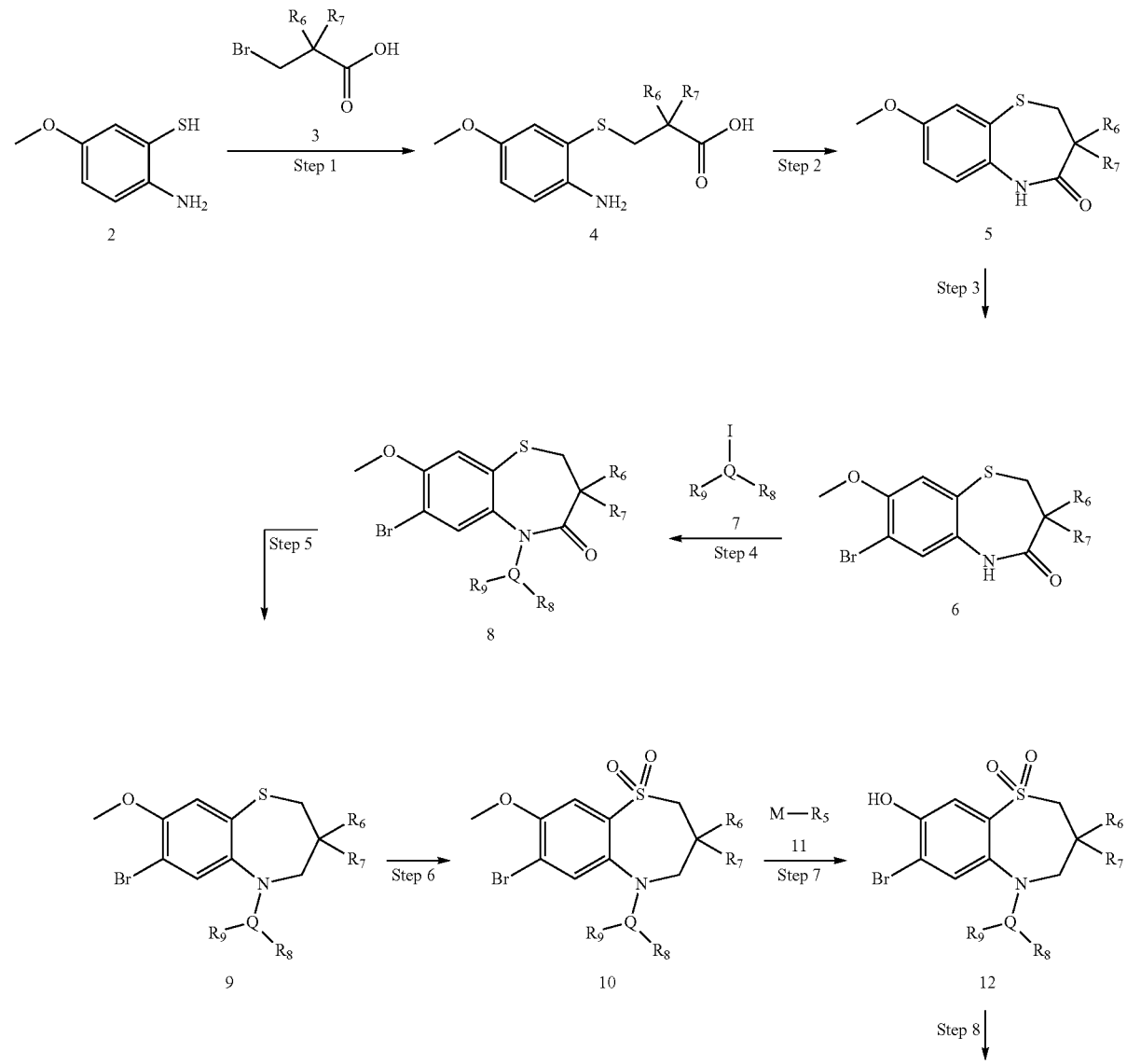

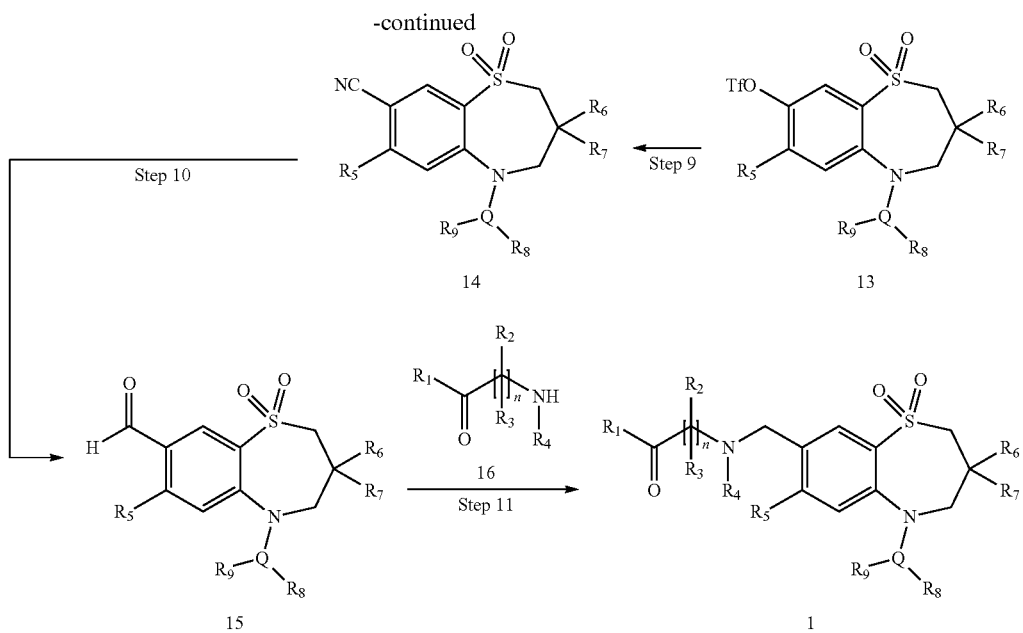

The substituents in the Reaction Scheme above are the same as defined previously.

Specifically, Step 1 relates to preparing a compound represented by Formula 4 by reacting amino-alkoxybenzenethiol (e.g., amino-methoxybenzenethiol), which is a compound represented by Formula 2, and a 3-bromo-2-(mono or di)alkylpropanoic acid derivative (e.g., 3-bromo-2,2-dibutylpropanoic acid, a.k.a. 2-bromomethyl-2-butyl-hexanoate), which is a compound represented by Formula 3. Preferably, the reaction in Step 1 may be performed in the presence of potassium hydroxide, and water may be used as a solvent, but is not limited thereto.

Step 2 relates to cyclization for forming benzothiazepine, in which a 3,3-dialkyl-8-alkoxy-2,3-dihydrobenzo[b][1,4]thiazepine-4(5H)-one derivative represented by Formula 5 is prepared by reacting a compound represented by Formula 4, prepared in Step 1, with HATU (1-[bis(dimethylamino)methylene]-1H-1,2,3-triazolo[4,5-b]pyridinium 3-oxide hexafluorophosphate). Preferably, dichloromethane may be used as a solvent for Step 2, but is not limited thereto.

Step 3 relates to introducing a bromo group as a reactive substituent group, in which a 7-bromo-3,3-dialkyl-8-alkoxy-2,3-dihydrobenzo[b][1,4]thiazepine-4(5H)-one derivative represented by Formula 6 is prepared by reacting a compound represented by Formula 5, prepared in Step 2, with N-bromosuccinimide. Preferably, dichloromethane may be used as a solvent for Step 3, but is not limited thereto. N-halosuccinimide including other halogen atoms may be used instead of N-bromosuccinimide. For the halogen atom, any one which can provide a substituent capable of exhibiting sufficient reactivity in a subsequent substitution reaction may be used without limitation.

Step 4 relates to introducing a substituent group on a nitrogen atom of thiazepine ring, which can be achieved by reacting a compound represented by Formula 6, prepared in Step 3, with an iodinated compound represented by Formula 7. Preferably, the reaction of Step 4 may be performed in the presence of CuI, and xylene may be used as a solvent, but is not limited thereto.

Step 5 relates to removing a ketone group on the thiazepine ring by a reduction reaction, and LiAlH$_4$ may be used as a reducing agent, but is not limited thereto, and any reducing agent capable of converting —(C=O)— to —CH$_2$— by selectively reducing the ketone group on the thiazepine ring may be used without limitation. Preferably, diethyl ether may be used as a solvent for Step 5, but is not limited thereto.

Step 6 relates to preparing a dioxide derivative of thiazepine by oxidizing with osmium tetroxide, and preferably a mixed solvent of tetrahydrofuran and t-butanol may be used as a solvent for Step 6, but is not limited thereto.

Step 7 relates to converting the alkoxy group on a benzo ring into a hydroxyl group while introducing a substituent group R$_5$ at the position, in which a reactive halogen is substituted by a substitution reaction, and a metal salt, for example, an alkali metal salt (M-R$_5$; M is an alkali metal) of the substituent group to be introduced may be used as a reactant for the substitution reaction. Preferably, dimethylformamide (DMF) may be used as a solvent for Step 7, but is not limited thereto.

Step 8 relates to converting the hydroxy group on a benzo ring into trifluoromethanesulfonate (triflate; OTf), which is a good leaving group, and trifluoromethanesulfonic anhydride (TfO$_2$) may be used as a reactant for the introduction of OTf. Preferably, dichloromethane may be used as a solvent for Step 8, but is not limited thereto.

Step 9 relates to introducing a cyano group as a precursor of an aminomethyl group, in which a OTf group is substituted with a CN group by reacting a compound represented by Formula 13, which is introduced with the OTf group and prepared in Step 8, with zinc cyanide. Preferably, the reaction of Step 9 may be performed in the presence of palladium, and dimethylformamide may be used as a solvent, but is not limited thereto.

Step 10 relates to converting a cyano group into a formyl group by reacting the compound in which the cyano group is introduced in Step 9 with diisobutylaluminum hydride (DIBAL-H). Preferably, dichloromethane may be used as a solvent for Step 10, but is not limited thereto.

Step 11 relates to obtaining a title compound by a condensation reaction between a compound represented by Formula 15, prepared in Step 10, and an amine derivative. Preferably, the reaction in Step 11 may be performed in the presence of sodium triacetoxyborohydride (NaB(OAc)$_3$H), and dichloroethane may be used as a solvent, but is not limited thereto.

In another aspect, the present invention provides a pharmaceutical composition for preventing or treating constipation comprising the compound represented by Formula 1 or a pharmaceutically acceptable salt thereof as an active ingredient.

As used herein, the term "prevention" refers to any action resulting in suppression or delay of the onset, spread, and recurrence of constipation due to the administration of the pharmaceutical composition according to the present invention, and the term "treatment" refers to any action resulting in improvement in symptoms of the disease(s) or the beneficial alteration from the administration of the composition according to the present invention.

The pharmaceutical composition of the present invention may comprise the compound represented by Formula 1 or a pharmaceutically acceptable salt thereof as an active ingredient, and also may further comprise a pharmaceutically acceptable carrier, diluent, or excipient.

The composition of the present invention is administered in a pharmaceutically effective amount. As used herein, the term "pharmaceutically effective amount" refers to an amount sufficient for the treatment of diseases at a reasonable benefit/risk ratio applicable to a medical treatment without causing any adverse effects, and the term "administration" refers to introduction of a predetermined substance into a patient by a certain suitable method.

As used herein, the term "therapeutically effective amount", which was used in combination with active ingredients, refers to the amount of aminoalkylbenzothiazepine derivatives or pharmaceutically acceptable salts thereof, which are effective for the prevention or treatment of a subject disease(s).

The pharmaceutical composition of the present invention may further comprise other known drug(s) conventionally used for preventing or treating the disease(s), in addition to aminoalkylbenzothiazepine derivatives or pharmaceutically acceptable salts thereof, as active ingredient(s), depending on the disease(s) to be prevented or treated.

Advantageous Effects

The novel aminoalkylbenzothiazepine derivatives of the present invention can inhibit the resorption of bile acid and thus allow bile acid to move to the large intestine, thereby inducing water secretion within the large intestine and promoting the movement of the large intestine. These results indicate that the compounds of the present invention can be effectively used in treating and preventing constipation.

BEST MODE

Hereinafter, the present invention will be described in more detail with reference to the following Examples. However, these Examples are for illustrative purposes only, and the invention is not intended to be limited by these Examples.

Various methods for synthesizing the starting materials to synthesize the compounds of the present invention have been known, and if available on the market, the starting materials may be purchased from the providers. Examples of the reagents suppliers include Sigma-Aldrich, TCI, Wako, Kanto, Fluorchem, Acros, Alfa, Fluka, and Dae-Jung, but are not limited thereto. Additionally, all the materials on the commercial market were used without further purification, unless specified otherwise.

First, the compounds used for syntheses in Examples were prepared as described in Preparation Examples. Preparation Examples are exemplary embodiments of Reaction Scheme 1, and may be appropriately adjusted corresponding to the structures of the compounds in Examples.

Preparation Example 1: Preparation of 3,3-dibutyl-7-methylthio-5-phenyl-2,3,4,5-tetrahydrobenzo[b][1,4]thiazepine-8-carbaldehyde 1,1-dioxide Step 1) Preparation of 2-(((2-amino-5-methoxyphenyl)thio)methyl)-2-butylhexanoic acid

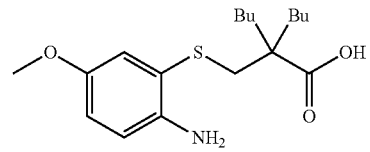

6-Methoxybenzo[d]thiazol-2-amine (25 g, 139.7 mmol) was added to 250 mL of 30% potassium hydroxide and stirred at 140° C. for 18 hours. The reaction mixture was checked with TLC to confirm the formation of 2-amino-5-methoxybenzenethiol, and cooled to room temperature. Then, 2-bromomethyl-2-butylhexanoate (44.6 g, 167.7 mmol) was added thereto and stirred at room temperature for about 17 hours. A saturated ammonium chloride solution and dichloromethane were added thereto, stirred for 10 minutes, and the dichloromethane layer was extracted, and this entire process was repeated three times. The dichloromethane layer was dried over anhydrous magnesium sulfate, filtered, and then concentrated. The thus-obtained concentrated compound was charged with t-butyl methyl ether and 6 N HCl solution to extract an ester layer and then concentrated again. The concentrated compound was a brown solid, and hexane was added thereto, stirred, and filtered to obtain 25 g of an ivory solid with 51% yield.

Step 2) Preparation of 7-bromo-3,3-dibutyl-8-methoxy-2,3-dihydrobenzo[b][1,4]thiazepine-4(5H)-one

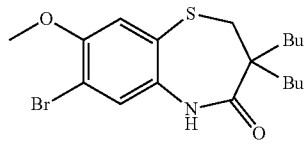

2-(((2-Amino-5-methoxyphenyl)thio)methyl)-2-butylhexanoic acid (25 g, 71.78 mmol) obtained in Step 1) was added to 900 mL of dichloromethane and cooled to −40° C. When the temperature reached −40° C., 1-[bis(dimethylamino)methylene]-1H-1,2,3-triazolo[4,5-b]pyridinium 3-oxide hexafluorophosphate (41 g, 107.68 mmol; HATU) was slowly added thereto and stirred for about 10 minutes. Then, diisopropylamine (58.15 mL, 358.9 mmol) was added slowly dropwise thereto. Upon completion of the addition of diisopropylamine, the mixture was stirred for about 5 hours. A saturated ammonium chloride solution was added thereto and the dichloromethane layer was extracted, and this entire process was repeated three times. The extracted dichloromethane layer was dried over anhydrous magnesium sulfate, filtered, and then concentrated to obtain 23 g of 3,3-dibutyl-8-methoxy-2,3-dihydrobenzo[b][1,4]thiazepine-4(5H)-one. The thus-obtained compound was charged with 480 mL of dichloromethane and cooled to 0° C. Upon cooling, N-bromosuccinimide (14.51 g, 81.54 mmol) was slowly added thereto and stirred for about 4 hours. Then, a saturated ammonium chloride solution was added thereto and the dichloromethane layer was extracted. The extracted dichloromethane layer was dried over anhydrous magnesium sulfate, filtered, and concentrated. The concentrated compound was charged with 200 mL of a mixture of hexane and ethyl acetate (hexane:ethyl acetate=30:1) and further charged with 200 mL of hexane while stirring, and the resulting solid was filtered to obtain 14 g of 7-bromo-3,3-dibutyl-8-methoxy-2,3-dihydrobenzo[b][1,4]thiazepine-4(5H)-one as a title compound, with 50% yield.

$^1$H NMR (400 MHz, CDCl$_3$) δ 7.58 (s, 1H), 6.99 (d, J=2.8 Hz, 1H), 6.87 (d, J=8.8 Hz, 1H), 6.77 (dd, J=8.8 Hz, 2.8 Hz, 1H), 3.78 (s, 3H), 2.97 (s, 2H), 1.78-1.85 (m, 2H), 1.55-1.62 (m, 2H), 1.18-1.30 (m, 8H), 0.87 (t, J=6.8 Hz, 6H).

Step 3) Preparation of 3,3-dibutyl-8-hydroxy-7-methylthio-5-phenyl-2,3,4,5-tetrahydrobenzo[b][1,4]thiazepine dioxide

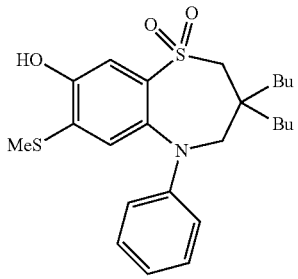

7-Bromo-3,3-dibutyl-8-methoxy-2,3-dihydrobenzo[b][1,4]thiazepine-4(5H)-one (5.77 g, 14.44 mmol) obtained in Step 2) was charged with iodobenzene (50 mL), copper iodide (0.55 g, 2.89 mmol), potassium carbonate (4 g, 28.9 mmol), and tris[2-(2-methoxyethoxy)ethyl]amine (0.5 mL, 1.44 mmol), stirred at room temperature for about 5 minutes, and refluxed at 190° C. for 17 hours. The resultant was cooled to room temperature, filtered with silica, and washed with hexane to remove iodobenzene. The silica-captured compound was eluted with ethyl acetate and dichloromethane, and the recovered solution was concentrated to obtain 5.8 g of 7-bromo-3,3-dibutyl-8-methoxy-5-phenyl-2,3-dihydrobenzo[b][1,4]thiazepine-4(5H)-one. Lithium aluminum hydride (1.4 g, 36.88 mmol) was added to a 500 mL round-bottom flask and dried under vacuum. Diethyl ether (150 mL) was added thereto, cooled to −10° C., and then anhydrous sulfate (1 mL, 18.44 mmol) was added slowly dropwise thereto. The thus-obtained 7-bromo-3,3-dibutyl-8-methoxy-5-phenyl-2,3-dihydrobenzo[b][1,4]thiazepine-4(5H)-one was dissolved in diethyl ether and added dropwise to the reaction flask. The resultant was stirred at room temperature for 2 hours, and charged with a saturated ammonium chloride solution to extract the diethyl ether layer. The extract was dried over anhydrous magnesium sulfate, filtered, and concentrated to obtain 5 g of 7-bromo-3,3-dibutyl-8-methoxy-5-phenyl-2,3,4,5-tetrahydrobenzo[b][1,4]thiazepine. The thus-obtained compound (5 g, 10.98 mmol) was charged with 75 mL of a mixed solvent (tetrahydrofuran:t-butanol=1:1), osmium tetroxide (0.07 g, 0.27 mmol), and N-methylmorpholine N-oxide (3.96 g, 32.94 mmol), and stirred at room temperature for 12 hours. A saturated ammonium chloride solution and dichloromethane were added thereto to extract the dichloromethane layer, and the extract was concentrated to obtain 3.55 g of 7-bromo-3,3-dibutyl-8-methoxy-5-phenyl-2,3,4,5-tetrahydrobenzo[b][1,4]thiazepine dioxide as an ivory solid. The thus-obtained compound (3.55 g, 7.18 mmol) was charged with dimethylformamide (100 mL), sodium thiomethoxide (5.032 g, 71.79 mmol), and sodium borohydride (5.43 g, 143.6 mmol), and stirred at 60° C. for 15 hours. A saturated ammonium chloride solution and t-butyl methyl ether were added thereto to extract the ether layer, and this was concentrated. The concentrated compound was charged with hexane, and the solid was filtered to obtain 2.7 g of 3,3-dibutyl-8-hydroxy-7-methylthio-5-phenyl-2,3,4,5-tetrahydrobenzo[b][1,4]thiazepine dioxide, with 84% yield.

$^1$H NMR (400 MHz, CDCl$_3$) δ 7.31 (s, 1H), 7.16 (t, J=8 Hz, 2H), 6.92 (d, J=8 Hz, 2H), 6.84 (t, J=6.8 Hz, 1H), 6.67 (s, 1H), 3.61 (s, 2H), 3.07 (s, 2H), 2.15 (s, 3H), 1.28-1.44 (m, 4H), 1.97-1.19 (m, 8H), 0.74 (t, J=6.8 Hz).

Step 4) Preparation of 3,3-dibutyl-7-methylthio-1,1-dioxido-5-phenyl-2,3,4,5-tetrahydrobenzo[b][1,4]thiazepine-8-yl trifluoromethanesulfonate

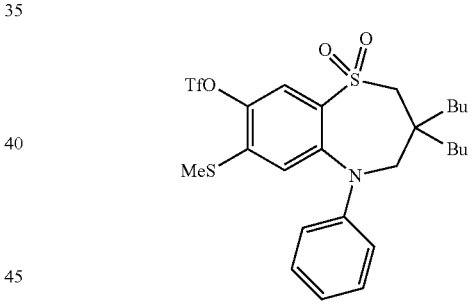

3,3-Dibutyl-8-hydroxy-7-methylthio-5-phenyl-2,3,4,5-tetrahydrobenzo[b][1,4]thiazepine dioxide (2.7 g, 5.98 mmol) obtained in Step 3) was charged with dichloromethane (30 mL) and pyridine (0.63 mL, 7.77 mmol), and cooled to 0° C. Trifluoromethanesulfonic anhydride (1.3 mL, 7.77 mmol) was added slowly dropwise thereto and stirred at room temperature for 5 hours. A saturated ammonium chloride solution was added thereto to extract the dichloromethane layer, and then dried over anhydrous magnesium sulfate, filtered, and concentrated. The resultant was purified by silica column chromatography using a mixed solvent (hexane:ethyl acetate=8:1). As a result, 2.96 g of 3,3-dibutyl-7-methylthio-1,1-dioxido-5-phenyl-2,3,4,5-tetrahydrobenzo[b][1,4]thiazepine-8-yl trifluoromethanesulfonate was obtained, with 86% yield.

$^1$H NMR (400 MHz, CDCl$_3$) δ 7.81 (s, 1H), 7.39 (t, J=7.6 Hz, 2H), 7.21 (d, J=7.6 Hz, 2H), 7.18 (d, J=7.2 Hz, 1H), 6.46 (s, 1H), 3.89 (s, 2H), 3.26 (s, 2H), 2.13 (s, 3H), 1.48-1.85 (m, 2H), 1.35-1.42 (m, 2H), 1.01-1.20 (m, 8H), 0.74 (t, J=6.8 Hz).

Step 5) Preparation of 3,3-dibutyl-7-methylthio-5-phenyl-2,3,4,5-tetrahydrobenzo[b][1,4]thiazepine-8-carbonitrile dioxide

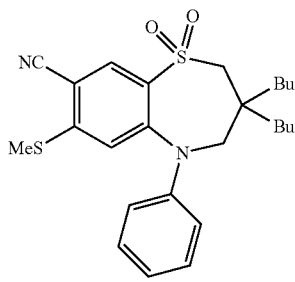

3,3-Dibutyl-7-methylthio-1,1-dioxido-5-phenyl-2,3,4,5-tetrahydrobenzo[b][1,4]thiazepine-8-yl trifluoromethanesulfonate (2.96 g, 5.12 mmol) obtained in Step 4) was charged with dimethylformamide (60 mL), zinc powder (0.034 g, 0.512 mmol), zinc cyanide (0.66 g, 5.632 mmol), tris(dibenzylideneacetone)dipalladium (0.47 g, 0.51 mmol), and 1,1-bis(diphenylphosphino)ferrocene (0.34 g, 0.614 mmol), and stirred at 80° C. for 20 hours. The resultant was cooled to room temperature, and a saturated ammonium chloride solution and ethyl acetate were added to extract the ethyl acetate layer. The extracted ethyl acetate layer was dried over anhydrous magnesium sulfate, filtered, and concentrated. The concentrated compound was purified by silica column chromatography using a mixed solvent (hexane:ethyl acetate=6:1) to obtain 1 g of the title compound, with 50% yield.

$^1$H NMR (400 MHz, CDCl$_3$) δ 8.19 (s, 1H), 7.45 (t, J=7.6 Hz, 2H), 7.24-7.31 (m, 3H), 6.26 (s, 1H), 4.02 (s, 2H), 3.30 (s, 2H), 2.11 (s, 3H), 1.26-1.58 (m, 4H), 0.83-1.19 (m, 8H), 0.74 (t, J=6.8 Hz).

Step 6) Preparation of 3,3-dibutyl-7-methylthio-5-phenyl-2,3,4,5-tetrahydrobenzo[b][1,4]thiazepine-8-carbaldehyde dioxide

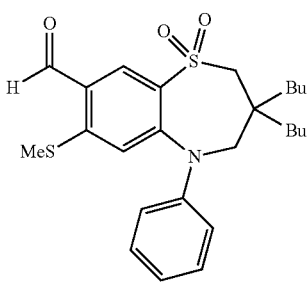

3,3-Dibutyl-7-methylthio-5-phenyl-2,3,4,5-tetrahydrobenzo[b][1,4]thiazepine-8-carbonitrile dioxide (1 g, 2.1 mmol) obtained in Step 5) was charged with dichloromethane, cooled to 0° C., and 5 mL of diisobutylaluminum hydride (DIBAL-H) was added slowly dropwise thereto. The resultant was heated to room temperature and stirred for 1 hour. Then, the resultant was again cooled to 0° C., charged with distilled water, ethyl acetate, and sodium potassium tartrate, and stirred for 30 minutes. After extracting the ethyl acetate layer, this was dried over anhydrous magnesium sulfate, filtered, and concentrated. The concentrated compound was purified by silica column chromatography using a mixed solvent (hexane:ethyl acetate=4:1) to obtain 600 mg of the title compound, with 63% yield.

$^1$H NMR (400 MHz, CDCl$_3$) δ 9.91 (s, 1H), 8.37 (s, 1H), 7.46 (t, J=7.6 Hz, 2H), 7.26-7.30 (m, 3H), 6.27 (s, 1H), 4.08 (s, 2H), 3.34 (s, 2-1), 0.88-1.40 (m, 12H), 0.77 (t, J=6.8 Hz).

Example 1: Preparation of 2-(((3,3-dibutyl-7-methylthio-1,1-dioxido-5-phenyl-2,3,4,5-tetrahydrobenzo[b][1,4]thiazepine-8-yl)methyl)amino)acetic acid

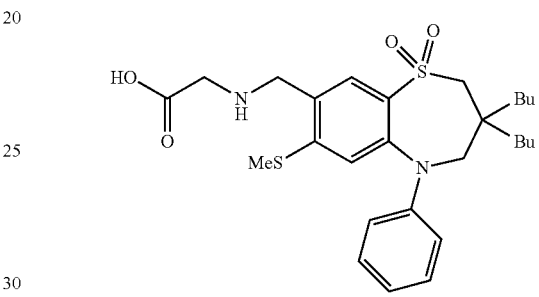

3,3-Dibutyl-7-methylthio-5-phenyl-2,3,4,5-tetrahydrobenzo[b][1,4]thiazepine-8-carbaldehyde dioxide (31 mg, 0.067 mnol) obtained in Preparation Example 1 was added to 2 mL of dichloroethane, and ethyl glycine methyl ester hydrochloride (11 mg, 0.088 mmol) was added thereto, and stirred at room temperature for 20 minutes. Then, sodium triacetoxyborohydride (28 mg, 0.131 mmol) was added thereto and stirred at room temperature for 17 hours. Upon completion of the reaction, an extraction was performed by adding dichloromethane and distilled water, dried over anhydrous magnesium sulfate, filtered, and concentrated under reduced pressure. The filtrate was purified with PTLC (dichloromethane:methanol=50:1) to obtain 20.5 mg of ethyl 2-(((3,3-dibutyl-7-methylthio-1,1-dioxido-5-phenyl-2,3,4,5-tetrahydrobenzo[b][1,4]thiazepine-8-yl)methyl)amino)acetate, with 57% yield.

The thus-obtained compound (20.5 mg, 0.038 mmol) was added to 3 mL of a mixed solution (tetrahydrofuran:methanol:distilled water=1:1:1), charged with lithium hydroxide (16 mg, 0.40 mmol), and stirred at room temperature for 12 hours. Upon completion of the reaction, ethyl acetate and 1 N HCl were added thereto for extraction, and the extract was dried over anhydrous magnesium sulfate, filtered, and concentrated under reduced pressure. The filtrate was purified with PTLC (dichloromethane:methanol=20:1) to obtain 10 mg of 2-(((3,3-dibutyl-7-methylthio-1,1-dioxido-5-phenyl-2,3,4,5-tetrahydrobenzo[b][1,4]thiazepine-8-yl)methyl)amino)acetic acid as the title compound (yield: 44%).

$^1$H NMR (400 MHz, CDCl$_3$) δ 8.22 (s, 1H), 7.34 (t, J=7.6 Hz, 2H), 7.24 (t, J=7.6 Hz, 2H), 7.12 (t, J=7.6 Hz, 1H), 6.47 (s, 1H), 4.46 (s, 2H), 3.73-3.93 (m, 4H), 3.33 (s, 2H), 2.15 (s, 3H), 1.47-1.52 (m, 2H), 1.33-1.39 (m, 2H), 1.08-1.15 (m, 4H), 1.00-1.03 (m, 4H), 0.78 (t, J=6.8 Hz, 6H).

Example 2: Preparation of 3-(((3,3-dibutyl-7-methylthio-1,1-dioxido-5-phenyl-2,3,4,5-tetrahydrobenzo[b][1,4]thiazepine-8-yl)methyl)amino)propanoic acid

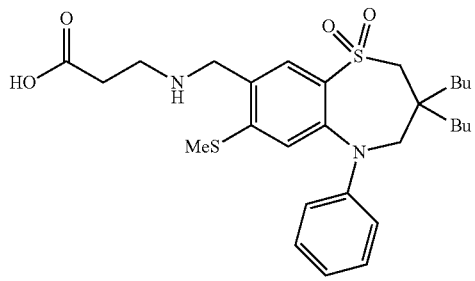

The title compound was synthesized in a manner similar to that of Example 1, except that ethyl 3-aminopropanoate was used as a reactant instead of ethyl glycine methyl ester hydrochloride (yield: 65%).

$^1$H NMR (400 MHz, CDCl$_3$) δ 8.14 (s, 1H), 7.38-7.34 (m, 2H), 7.26-7.22 (m, 2H), 7.17-6.97 (m, 1H), 6.46 (s, 1H), 4.35 (s, 2H), 3.88 (s, 2H), 3.26 (s, 4H), 2.93 (s, 2H), 2.15 (s, 3H), 1.60-1.46 (m, 2H), 1.40-1.29 (m, 2H), 1.14-0.99 (m, 8H), 0.81-0.74 (m, 6H).

Example 3: Preparation of 2-(((3,3-dibutyl-7-methylthio-1,1-dioxido-5-phenyl-2,3,4,5-tetrahydrobenzo[b][1,4]thiazepine-8-yl)methyl)amino)succinic acid

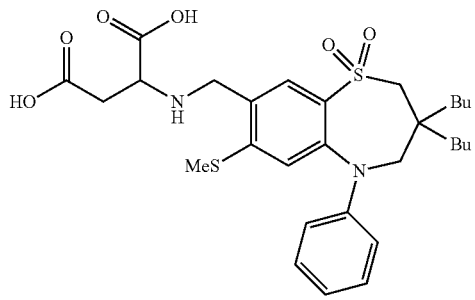

The title compound was synthesized in a manner similar to that of Example 1, except that diethyl aspartate was used as a reactant instead of ethyl glycine methyl ester hydrochloride (yield: 52%).

1H NMR (400 MHz, CDCl$_3$) δ 8.21 (s, 1H), 7.34 (s, 3H), 7.24 (s, 1H), 7.12 (s, 1H), 6.46 (s, 1H), 4.62-4.35 (m, 2H), 4.02-3.88 (m, 2H), 3.50-3.10 (m, 5H), 2.17 (s, 3H), 1.66-1.35 (m, 4H), 1.22-0.89 (m, 8H), 0.75 (s, 6H).

Example 4: Preparation of (S)-2-(((3,3-dibutyl-7-methylthio-1,1-dioxido-5-phenyl-2,3,4,5-tetrahydrobenzo[b][1,4]thiazepine-8-yl)methyl)amino)propanoic acid

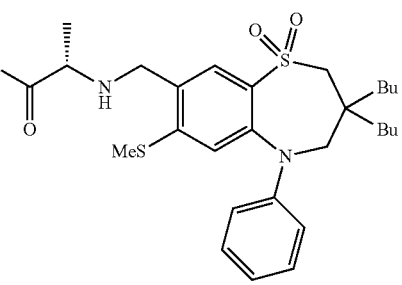

The title compound was synthesized in a manner similar to that of Example 1, except that diethyl alanine ester was used as a reactant instead of ethyl glycine methyl ester hydrochloride (yield: 61%).

$^1$H NMR (400 MHz, CDCl$_3$) δ 8.16 (s, 1H), 7.32 (s, 2H), 7.16-7.12 (m, 3H), 6.45 (s, 1H), 4.24-4.19 (m, 2H), 3.81 (s, 2H), 3.52 (s, 1H), 3.27 (s, 2H), 2.09 (s, 3H), 1.52-1.42 (m, 5H), 1.41-1.25 (m, 2H), 1.24-0.92 (m, 8H), 0.88-0.65 (m, 6H).

Example 5: Preparation of 2-(((3,3-dibutyl-7-methylthio-1,1-dioxido-5-phenyl-2,3,4,5-tetrahydrobenzo[b][1,4]thiazepine-8-yl)methyl)amino)pentanedioic acid

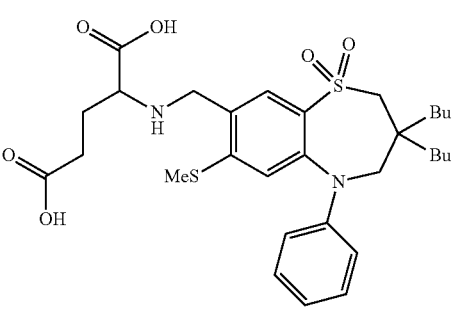

The title compound was synthesized in a manner similar to that of Example 1, except that diethyl glutamine ester was used as a reactant instead of ethyl glycine methyl ester hydrochloride (yield: 36%).

$^1$H NMR (400 MHz, CDCl$_3$) δ 7.74 (s, 1H), 7.35-7.33 (m, 2H), 7.19-7.18 (m, 2H), 7.12-7.09 (m, 1H), 6.43 (s, 1H), 4.97 (d, J=14 Hz, 1H), 4.17 (d, J=15.2 Hz, 1H), 3.85 (s, 3H), 3.26 (s, 2H), 1.21-0.96 (m, 8H), 0.82-0.76 (m, 6H).

Example 6: Preparation of 4-amino-2-(((3,3-dibutyl-7-methylthio-1,1-dioxido-5-phenyl-2,3,4,5-tetrahydrobenzo[b][1,4]thiazepine-8-yl)methyl)amino)-4-oxobutanoic acid

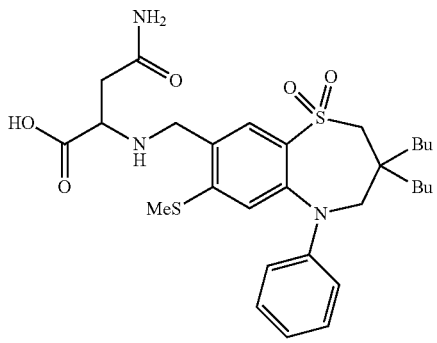

The title compound was synthesized in a manner similar to that of Example 1, except that diethyl arginine ester was used as a reactant instead of ethyl glycine methyl ester hydrochloride (yield: 23%).

MS: 576.25 [M+H]+.

Example 7: Preparation of (R)-2-(((3,3-dibutyl-7-methylthio-1,1-dioxido-5-phenyl-2,3,4,5-tetrahydrobenzo[b][1,4]thiazepine-8-yl)methyl)amino)propanoic acid

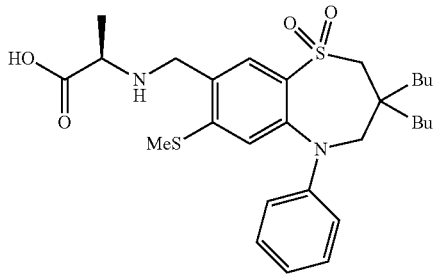

The title compound was synthesized in a manner similar to that of Example 1, except that diethyl alanine ester was used as a reactant instead of ethyl glycine methyl ester hydrochloride (yield: 56%).

$^1$H NMR (400 MHz, CDCl$_3$) δ 8.00 (s, 1H), 7.19-7.26 (m, 2H), 7.08-7.10 (m, 3H), 6.38 (s, 1H), 4.03-7.09 (m, 2H), 3.76 (s, 2H), 3.41 (s, 1H), 3.20 (s, 2H), 2.89-2.99 (m, 1H), 2.02 (s, 3H), 1.43 (s, 3H), 1.29-1.36 (m, 2H), 1.18-1.23 (m, 2H), 0.81-1.08 (m, 8H), 0.69-0.7 (m, 6H).

Example 8: Preparation of 2-(((3,3-dibutyl-7-methylthio-1,1-dioxido-5-phenyl-2,3,4,5-tetrahydrobenzo[b][1,4]thiazepine-8-yl)methyl)amino)-2-methylpropanoic acid

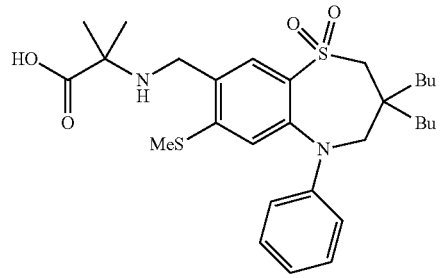

The title compound was synthesized in a manner similar to that of Example 1, except that ethyl 2-amino-2-methylpropanoate was used as a reactant instead of ethyl glycine methyl ester hydrochloride (yield: 57%).

$^1$H NMR (400 MHz, CDCl$_3$) δ 7.99 (s, 1H), 7.33 (t, J=7.6 Hz, 2H), 7.17-7.18 (m, 2H), 7.11-7.12 (m, 1H), 6.48 (s, 1H), 3.96 (s, 2H), 3.81 (s, 2H), 3.21 (s, 2H), 2.14 (s, 3H), 1.53 (s, 6H), 1.25-1.34 (m, 4H), 0.85-1.14 (m, 8H), 0.76 (t, J=6.8 Hz, 6H).

Example 9: Preparation of (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-imidazol-4-yl)propanoic acid

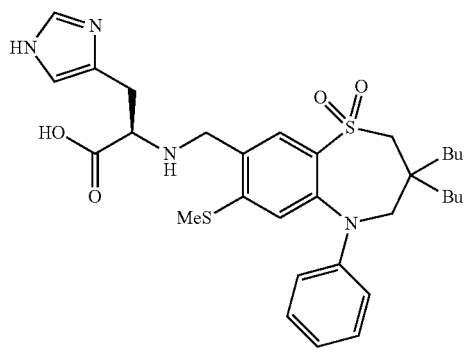

The title compound was synthesized in a manner similar to that of Example 1, except that ethyl histidine ester was used as a reactant instead of ethyl glycine methyl ester hydrochloride (yield: 43%).

$^1$H NMR (400 MHz, CDCl$_3$) δ 7.77 (s, 1H), 7.54 (s, 1H), 7.28-7.30 (m, 2H), 7.04-7.11 (m, 3H), 6.78 (s, 1H), 6.38 (s, 1H), 3.78 (s, 4H), 3.41-4.11 (m, 2H), 3.18 (s, 2H), 2.94-2.98 (m, 1H), 1.86 (s, 3H), 1.27-1.43 (m, 4H), 0.82-1.10 (m, 8H), 0.71 (t, J=6.8 Hz, 6H).

Example 10: Preparation of (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-indol-2-yl)propanoic acid

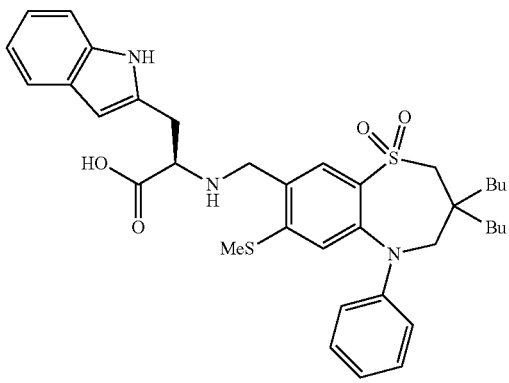

The title compound was synthesized in a manner similar to that of Example 1, except that ethyl tryptophan ester was used as a reactant instead of ethyl glycine methyl ester hydrochloride (yield: 37%).

MS: 648.29 [M+H]$^+$.

Example 11: Preparation of (S)-2-(((3,3-dibutyl-7-methylthio-1,1-dioxido-5-phenyl-2,3,4,5-tetrahydrobenzo I[b][1,4]thiazepine-8-yl)methyl)amino)-4-methylpentanoic acid

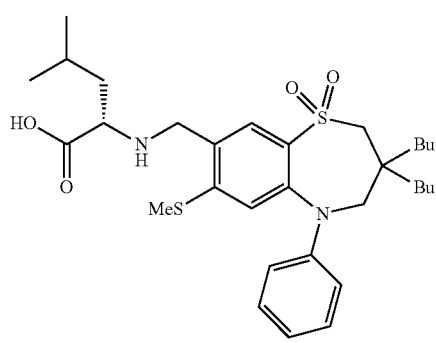

The title compound was synthesized in a manner similar to that of Example 1, except that ethyl leucine ester was used as a reactant instead of ethyl glycine methyl ester hydrochloride (yield: 58%).

MS: 575.29 [M+H]+.

Example 12: Preparation of (S)-2-(((3,3-dibutyl-7-methylthio-1,1-dioxido-5-phenyl-2,3,4,5-tetrahydrobenzo[b][1,4]thiazepine-8-yl)methyl)amino)pentanedioic acid

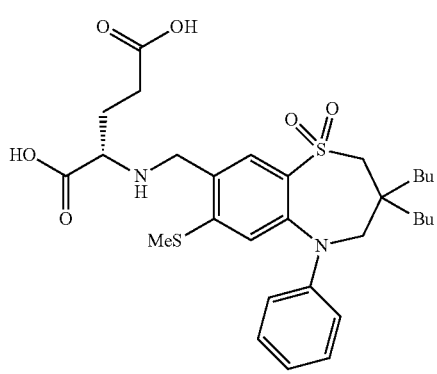

The title compound was synthesized in a manner similar to that of Example 1, except that diethyl glutamine ester was used as a reactant instead of ethyl glycine methyl ester hydrochloride (yield: 25%).

MS: 591.27 [M+H]$^+$.

Example 13: Preparation of (S)-2-(((3,3-dibutyl-7-methylthio-1,1-dioxido-5-phenyl-2,3,4,5-tetrahydrobenzo[b][1,4]thiazepine-8-yl)methyl)amino)-3-hydroxypropanoic acid The title compound was synthesized in a manner similar to that of Example 1, except that diethyl serine ester was used as a reactant instead of ethyl glycine methyl ester hydrochloride (yield: 45%).

MS: 549.25 [M+H]+.

Example 14: Preparation of 3-((carboxymethyl)((3,3-dibutyl-7-methylthio-1,1-dioxido-5-phenyl-2,3,4,5-tetrahydrobenzo[b][1,4]thiazepine-8-yl)methyl)amino)propanoic acid

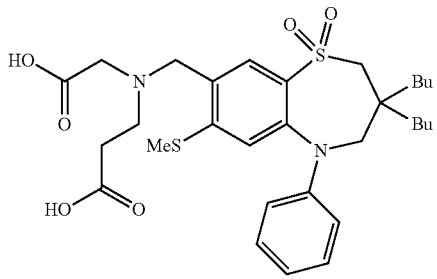

The title compound was synthesized in a manner similar to that of Example 1, except that 3-((2-ethoxy-2-oxoethyl)amino)propanoate was used as a reactant instead of ethyl glycine methyl ester hydrochloride (yield: 49%).

$^1$H NMR (400 MHz, CDCl$_3$) δ 8.16 (s, 1H), 7.34-7.43 (m, 2H), 7.27 (s, 2H), 7.12-7.16 (m, 1H), 6.45 (s, 1H), 4.60-4.72 (m, 2H), 4.48-4.59 (m, 2H), 4.00-4.13 (m, 2H), 3.34 (s, 2H), 3.12-3.23 (m, 2H), 2.14 (s, 3H), 1.36-1.60 (m, 4H), 1.24-1.30 (m, 8H), 0.71 (t, J=6.8 Hz, 6H).

Example 15: Preparation of 3-(((3,3-dibutyl-7-methylthio-1,1-dioxido-5-phenyl-2,3,4,5-tetrahydrobenzo[b][1,4]thiazepine-8-yl)methyl)amino)pentanedioic acid

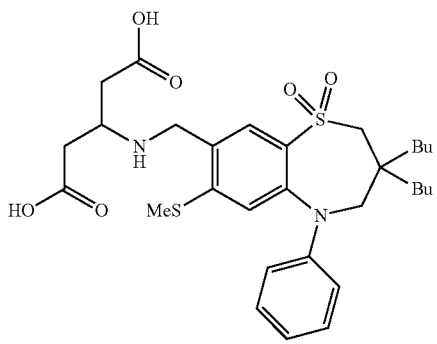

The title compound was synthesized in a manner similar to that of Example 1, except that diethyl 2,2'-azanediyldiacetate was used as a reactant instead of ethyl glycine methyl ester hydrochloride (yield: 41%).

$^1$H NMR (400 MHz, CDCl$_3$) δ 8.02 (s, 1H), 7.32 (t, J=7.6 Hz, 2H), 7.21 (d, J=7.2 Hz, 2H), 7.10 (t, J=6.8 Hz, 1H), 6.48 (s, 1H), 4.47 (s, 2H), 4.03 (s, 1H), 3.85 (m, 2H), 3.29 (s, 2H), 3.06-3.17 (m, 4H), 2.16 (s, 3H), 1.35-1.46 (m, 4H), 1.23-1.32 (m, 8H), 0.71 (t, J=6.8 Hz, 6H).

Example 16: Preparation of 2-(((3,3-dibutyl-7-methylthio-1,1-dioxido-5-phenyl-2,3,4,5-tetrahydrobenzo[b][1,4]thiazepine-8-yl)methyl)amino)-2-oxoacetic acid

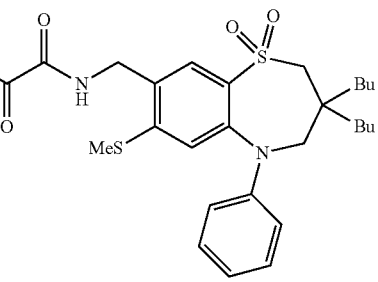

3,3-Dibutyl-7-methylthio-5-phenyl-2,3,4,5-tetrahydrobenzo[b][1,4]thiazepine-8-carbonitrile dioxide (160 mg, 0.350 mmol) obtained in Step 5) of Preparation Example 1 was dissolved in 5 mL of a mixed solution (dichloromethane:diethyl ether=3:2). The resultant was cooled to 0° C., and lithium aluminum hydride (66 mg, 1.752 mmol) was added in divided allocations, and stirred at room temperature for 12 hours. Upon completion of the reaction, diethyl ether and distilled water were added thereto for extraction, and the extract was dried over anhydrous magnesium sulfate, filtered, and concentrated under reduced pressure. The filtrate was purified with PTLC (dichloromethane:methanol=50:1) to obtain 40 mg of 8-aminomethyl-3,3-dibutyl-7-methylthio-5-phenyl-2,3,4,5-tetrahydrobenzo[b][1,4]thiazepine dioxide (yield: 25%).

The thus-obtained compound (0.023 g, 0.05 mmol) was added to 5 mL of dichloromethane, and triethylamine (0.01 mL, 0.1 mmol) and 4-dimethylaminopyridine (0.003 g) were added thereto and stirred at room temperature for 10 minutes. The reaction solution was cooled to 0° C., slowly charged with ethyl 2-chloro-2-oxoacetate, and stirred at room temperature for 18 hours. An ammonium chloride solution and dichloromethane were added thereto to extract the dichloromethane layer. The extracted dichloromethane layer was dried over anhydrous magnesium sulfate, filtered, and concentrated. The concentrated compound (0.02 g) was charged with tetrahydrofuran (1 mL), methanol (1 mL), distilled water (1 mL), and lithium hydroxide (0.03 g), and stirred at room temperature for 12 hours. Then, 6 N HCl and dichloromethane were added thereto for extraction followed by concentration, and the concentrated compound was purified with PTLC (dichloromethane:methanol=13:1) to obtain 0.015 g of 2-(((3,3-dibutyl-7-methylthio-1,1-dioxido-5-phenyl-2,3,4,5-tetrahydrobenzo[b][1,4]thiazepine-8-yl)methyl)amino)-2-oxoacetic acid as the title compound (yield: 78%).

$^1$H NMR (400 MHz, CDCl$_3$) δ 7.76 (s, 1H), 7.25-7.33 (m, 2H), 6.97-7.11 (m, 3H), 6.50 (s, 1H), 3.72-4.40 (m, 2H), 3.19 (s, 2H), 2.50-2.68 (m, 2H), 2.06 (s, 3H), 1.27-1.43 (m, 4H), 0.93-1.20 (m, 8H), 0.71 (t, J=6.8 Hz, 6H).

Example 17: Preparation of 1-(((3,3-dibutyl-7-methylthio-1,1-dioxido-5-phenyl-2,3,4,5-tetrahydrobenzo[b][1,4]thiazepine-8-yl)methyl)amino)cyclopropanecarboxylic acid

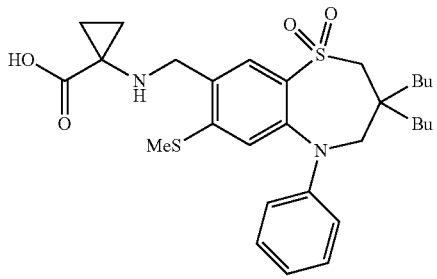

The title compound was synthesized in a manner similar to that of Example 1, except that ethyl 1-aminocyclopropane carboxylate was used as a reactant instead of ethyl glycine methyl ester hydrochloride (yield: 52%).

$^1$H NMR (400 MHz, CDCl$_3$) δ 8.11 (s, 1H), 7.42-7.35 (m, 2H), 7.21-7.15 (m, 2H), 7.13-7.12 (m, 1H), 6.49 (s, 1H), 4.53 (s, 2H), 3.88 (s, 2H), 3.24 (s, 2H), 2.04 (s, 3H), 1.68-1.61 (m, 2H), 1.55-1.48 (m, 2H), 1.21-0.92 (m, 12H), 0.78-0.71 (in, 6H).

Example 18: Preparation of 2-(((3,3-dibutyl-7-methylthio-1,1-dioxido-5-phenyl-2,3,4,5-tetrahydrobenzo[b][1,4]thiazepine-8-yl)methyl)amino)-2-oxoethanesulfonic acid

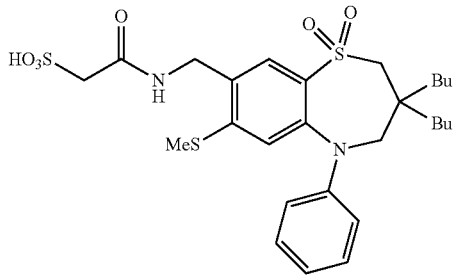

8-Aminomethyl-3,3-dibutyl-7-methylthio-5-phenyl-2,3,4,5-tetrahydrobenzo[b][1,4]thiazepine dioxide was prepared in the same manner as in Example 16. The compound (40 mg, 0.087 mmol) was dissolved in 4 mL of dichloromethane. The resultant was cooled to 0° C., triethylamine (36 μL, 0.260 mmol) was added slowly dropwise thereto, and stirred for 10 minutes. Bromoacetyl chloride (15 μL, 0.174 mmol) was added slowly dropwise thereto, and stirred at room temperature for 16 hours. Upon completion of the reaction, dichloromethane and an ammonium chloride solution were added thereto for extraction, and the extract was dried over anhydrous magnesium sulfate, filtered, and concentrated under reduced pressure. The filtrate was purified with PTLC (dichloromethane:methanol=30:1) to obtain mg of 2-bromo-N-((3,3-dibutyl-7-methylthio-1,1-dioxido-5-phenyl-2,3,4,5-tetrahydrobenzo[b][1,4]thiazepine-8-yl)methyl)acetamide (yield: 50%).

The thus-obtained compound (25 mg, 0.043 mmol) was dissolved in 3 mL of a mixed solution (ethanol:distilled water=1:1). Sodium sulfite (271 mg, 2.149 mmol) was added thereto and stirred at 80° C. for 17 hours. Upon completion of the reaction, the resultant was cooled to room temperature. Ethyl acetate and distilled water were added thereto for extraction, and the extract was dried over anhydrous magnesium sulfate, filtered, and concentrated under reduced pressure. The filtrate was purified with PTLC (dichloromethane:methanol=10:1) to obtain 12.5 mg of 2-(((3,3-dibutyl-7-methylthio-1,1-dioxido-5-phenyl-2,3,4,5-tetrahydrobenzo[b][1,4]thiazepine-8-yl)methyl)amino)-2-oxoethanesulfonic acid (yield: 50%).

MS: 583.20 [M+H]$^+$.

Example 19: Preparation of 2-(((3,3-dibutyl-5-(4-methoxyphenyl)-7-methylthio-1,1-dioxido-2,3,4,5-tetrahydrobenzo[b][1,4]thiazepine-8-yl)methyl)amino)acetic acid

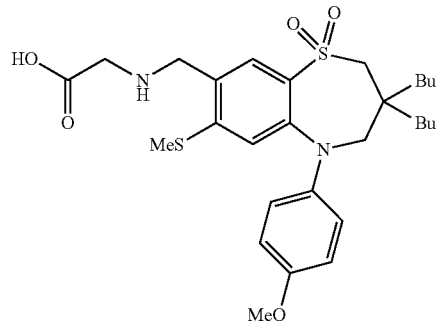

The title compound was synthesized in a manner similar to that of Example 1, except that 1-iodo-4-methoxybenzene was used in Step 3 of Preparation Example 1 instead of iodobenzene (yield: 64%).

$^1$H NMR (400 MHz, CDCl$_3$) δ 8.01 (s, 1H), 7.13-7.15 (m, 2H), 6.80-6.89 (m, 2H), 6.31 (s, 1H), 4.22 (s, 2H), 3.70-3.81 (m, 5H), 3.42 (s, 2H), 3.21 (s, 2H), 2.08 (s, 3H), 1.30-1.55 (m, 4H), 0.86-1.06 (m, 8H), 0.71-0.76 (m, 6H).

Example 20: Preparation of 2-(((3,3-dibutyl-5-(4-hydroxyphenyl)-7-methylthio-1,1-dioxido-2,3,4,5-tetrahydrobenzo[b][1,4]thiazepine-8-yl)methyl)amino)acetic acid

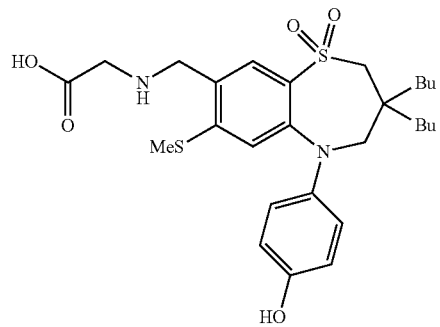

The title compound was synthesized in a manner similar to that of Example 1, except that 4-iodophenol was used in Step 3 of Preparation Example 1 instead of iodobenzene (yield: 37%).

¹H NMR (400 MHz, CDCl₃) δ 7.94 (s, 1H), 7.20 (d, J=8.8 Hz, 2H), 6.89 (d, J=8 Hz, 2H), 6.43 (s, 1H), 4.30 (s, 2H), 3.89-3.93 (m, 4H), 3.30-3.36 (m, 2H), 2.21 (s, 3H), 1.40-1.61 (m, 4H), 1.20-1.29 (m, 8H), 0.81 (t, J=6.8 Hz, 6H).

Example 21: Preparation of 2-(((3,3-dibutyl-5-(3-methoxyphenyl)-7-methylthio-1,1-dioxido-2,3,4,5-tetrahydrobenzo[b][1,4]thiazepine-8-yl)methyl)amino)acetic acid

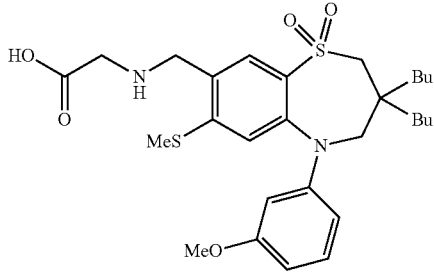

The title compound was synthesized in a manner similar to that of Example 1, except that 1-iodo-3-methoxybenzene was used in Step 3 of Preparation Example 1 instead of iodobenzene (yield: 47%).

¹H NMR (400 MHz, CDCl₃) δ 8.05 (s, 1H), 7.27-7.23 (m, 1H), 6.78-6.67 (m, 2H), 6.66-6.57 (m, 1H), 6.54 (s, 1H), 4.20 (s, 2H), 3.82 (s, 2H), 3.79 (s, 3H), 3.42 (s, 2H), 3.29 (s, 2H), 1.53-1.47 (m, 2H), 1.43-1.32 (m, 2H), 1.24-1.04 (m, 8H), 0.88-0.78 (m, 6H).

Example 22: Preparation of 2-(((3,3-dibutyl-5-(4-fluorophenyl)-7-methylthio-1,1-dioxido-2,3,4,5-tetrahydrobenzo[b][1,4]thiazepine-8-yl)methyl)amino)acetic acid

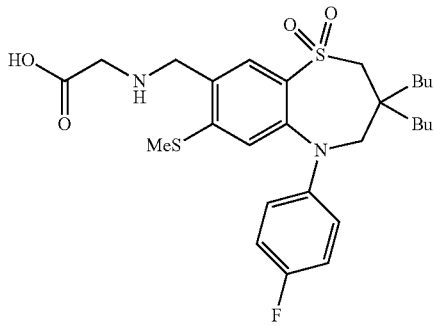

The title compound was synthesized in a manner similar to that of Example 1, except that 1-fluoro-4-iodobenzene was used in Step 3 of Preparation Example 1 instead of iodobenzene.

¹H NMR (400 MHz, CDCl₃) δ 8.12 (s, 1H), 7.17-7.20 (m, 2H), 7.03 (t, J=8.4 Hz, 2H), 6.40 (s, 1H), 4.16 (s, 2H), 3.70 (s, 2H), 3.33 (s, 2H), 3.21 (s, 2H), 2.08 (s, 3H), 1.37-1.46 (m, 4H), 0.82-1.06 (m, 8H), 0.77 (t, J=6.8 Hz, 6H).

Example 23: Preparation of 2-(((3,3-dibutyl-5-(3-fluorophenyl)-7-methylthio-1,1-dioxido-2,3,4,5-tetrahydrobenzo[b][1,4]thiazepine-8-yl)methyl)amino)acetic acid

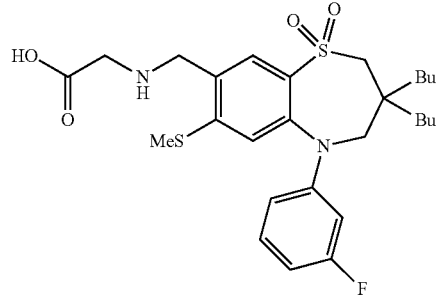

The title compound was synthesized in a manner similar to that of Example 1, except that 1-fluoro-3-iodobenzene was used in Step 3 of Preparation Example 1 instead of iodobenzene.

¹H NMR (400 MHz, CDCl₃) δ 8.15 (s, 1H), 7.23-7.13 (m, 1H), 6.89-6.83 (m, 2H), 6.75-6.71 (m, 1H), 6.65 (s, 1H), 4.27 (s, 2H), 3.73 (s, 2H), 3.52 (s, 2H), 3.26 (s, 2H), 2.20 (s, 3H), 1.57-1.46 (m, 2H), 1.43-1.33 (m, 2H), 1.26-1.07 (m, 8H), 0.86-0.78 (m, 6H).

Example 24: Preparation of 2-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)acetic acid

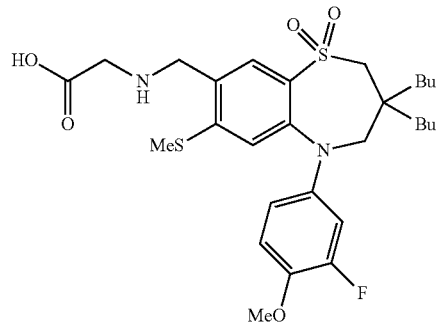

The title compound was synthesized in a manner similar to that of Example 1, except that 2-fluoro-4-iodo-1-methoxybenzene was used in Step 3 of Preparation Example 1 instead of iodobenzene.

¹H NMR (400 MHz, CDCl₃) δ 8.10 (brs, 1H), 6.70-6.90 (brs, 3H), 6.30-6.50 (brs, 1H), 3.90-4.20 (brs, 2H), 3.30-3.89 (brs, 3H), 3.55-3.29 (brs, 2H), 3.45-2.95 (m, 4H), 1.98-2.22 (brs, 3H), 1.23-1.49 (m, 4H), 0.73-1.24 (8H), 0.73 (brs, 6H).

Example 25: Preparation of 2-(((3,3-dibutyl-5-(4-methoxyphenyl)-7-methylthio-1,1-dioxido-2,3,4,5-tetrahydrobenzo[b][1,4]thiazepine-8-yl)methyl)amino)-2-oxoethanesulfonic acid

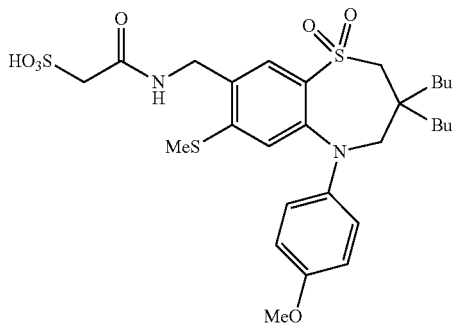

The title compound was synthesized in a manner similar to that of Example 18, except that 1-iodo-4-methoxybenzene was used in Step 3 of Preparation Example 1 instead of iodobenzene.

$^1$H NMR (400 MHz, CDCl$_3$) δ 7.70 (s, 1H), 7.09-6.94 (m, 2H), 6.82-6.64 (m, 2H), 6.27 (s, 1H), 3.80-3.63 (m, 7H), 3.12 (s, 2H), 2.43 (s, 2H), 1.97 (s, 3H), 1.52-1.27 (m, 4H), 1.07-0.88 (m, 8H), 0.82-0.78 (m, 6H).

Example 26: Preparation of 1-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)cyclopropanecarboxylic acid

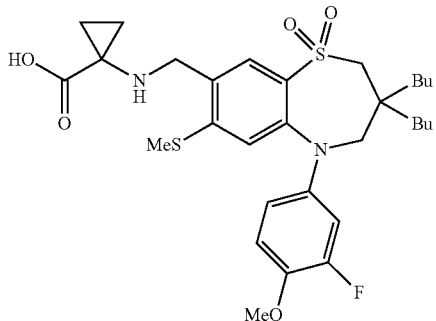

The title compound was synthesized in a manner similar to that of Example 17, except that 2-fluoro-4-iodo-1-methoxybenzene was used in Step 3 of Preparation Example 1 instead of iodobenzene.

$^1$H NMR (400 MHz, CDCl$_3$) δ 7.89 (s, 1H), 6.98-6.82 (m, 3H), 6.48 (s, 1H), 3.97 (s, 2H), 3.88 (s, 3H), 3.70 (s, 2H), 3.19 (s, 2H), 2.17 (s, 3H), 1.51-1.32 (m, 4H), 1.20-0.94 (m, 8H), 0.81-0.78 (m, 6H).

Example 27: Preparation of 2-(((3,3-dibutyl-5-(4-fluorophenyl)-7-methylthio-1,1-dioxido-2,3,4,5-tetrahydrobenzo[b][1,4]thiazepine-8-yl)methyl)amino)-2-oxoacetic acid

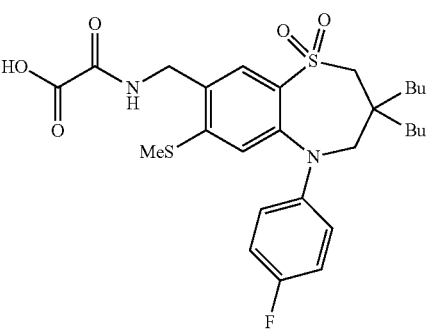

The title compound was synthesized in a manner similar to that of Example 16, except that 1-fluoro-4-iodobenzene was used in Step 3 of Preparation Example 1 instead of iodobenzene.

$^1$H NMR (400 MHz, CDCl$_3$) δ 7.72 (s, 1H), 7.10 (brs, 2H), 6.95 (brs, 2H), 6.42 (s, 1H), 4.22-4.36 (m, 2H), 3.66-3.97 (m, 2H), 3.19-3.47 (m, 2H), 2.07 (s, 3H), 1.30-1.33 (m, 4H), 0.88-1.12 (m, 8H), 0.75-0.83 (m, 3H).

Example 28: Preparation of (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)propanoic acid

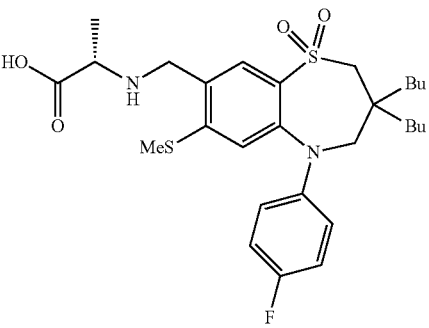

The title compound was synthesized in a manner similar to that of Example 4, except that 1-fluoro-4-iodobenzene was used in Step 3 of Preparation Example 1 instead of iodobenzene.

$^1$H NMR (400 MHz, CDCl$_3$) δ 7.72 (s, 1H), 7.10 (brs, 2H), 6.95 (brs, 2H), 6.42 (s, 1H), 4.22-4.36 (m, 2H), 3.66-3.97 (m, 2H), 3.19-3.47 (m, 2H), 2.07 (s, 3H), 1.30-1.33 (m, 4H), 0.88-1.12 (m, 8H), 0.75-0.83 (m, 3H).

Example 29: Preparation of (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)-3-hydroxypropanoic acid

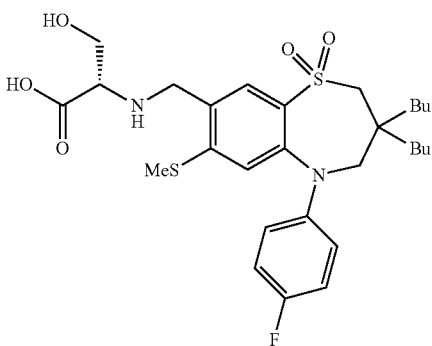

The title compound was synthesized in a manner similar to that of Example 13, except that 1-fluoro-4-iodobenzene was used in Step 3 of Preparation Example 1 instead of iodobenzene.

$^1$H NMR (400 MHz, CDCl$_3$) δ 8.15 (s, 1H), 7.17 (brs, 2H), 6.95 (brs, 2H), 6.51 (s, 1H), 4.36 (brs, 2H), 3.95 (brs, 2H), 6.63 (brs, 2H), 3.46 (s, 1H), 3.26 (brs, 2H), 2.01 (s, 3H), 1.25-1.43 (m, 4H), 0.70-0.87 (m, 8H), 0.59-0.67 (m, 3H).

Example 30: Preparation of 1-(((3,3-dibutyl-5-(4-fluorophenyl)-7-methylthio-1,1-dioxido-2,3,4,5-tetrahydrobenzo[b][1,4]thiazepine-8-yl)methyl)amino)cyclopropanecarboxylic acid

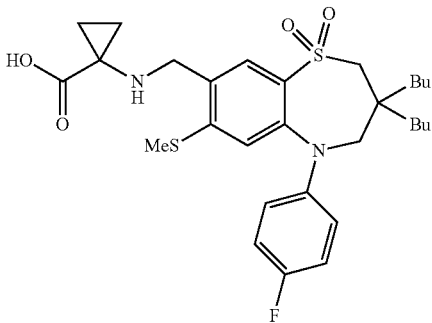

The title compound was synthesized in a manner similar to that of Example 17, except that 1-fluoro-4-iodobenzene was used in Step 3 of Preparation Example 1 instead of iodobenzene.

$^1$H NMR (400 MHz, CDCl$_3$) δ 7.92 (s, 1H), 7.17-7.14 (m, 2H), 7.09-7.02 (m, 2H), 6.42 (s, 1H), 4.11 (s, 2H), 3.77 (s, 2H), 3.22 (s, 2H), 2.15 (s, 3H), 1.68-1.46 (m, 4H), 1.40-1.30 (m, 4H), 1.21-0.92 (m, 8H), 0.88-0.76 (in, 6H).

Experimental Example 1: Feces Excretion Time and Evaluation of Efficiency

Eight-week-old SD rats were purchased and allowed to adapt to breeding conditions under 12-hour illumination at 24° C. for 7 days. The rats were made to fast for 16 hours before the experimental day, and orally administered on the experimental day with a vehicle (0.5% methylcellulose) and a test material, which were prepared at a concentration of 0.2 mg/mL and a dose of 5 mg/kg, respectively. Thirty minutes after the administration, the rats fed with 3 g of a barium-containing diet were placed into a metabolism cage and observed to record the time required for the barium to be excreted as feces in each rat after being passed through the intestines for 10 hours. Additionally, the percentage of rats that excreted barium-containing feces within 10 hours were calculated, and the results are shown in Table 1 below.

TABLE 1

| Example | Feces excretion time (min) @ volume (mg/kg) | Percentage of subjects excreting feces within 10 hours (%) |
|---|---|---|
| Vehicle | D | C |
| 1 | C @ 0.1 | B @ 0.1 |
|  | B @ 1 | A @ 1 |
|  | A @ 5 | A @ 5 |
| 18 | B @ 1 | B @ 1 |
| 19 | C @ 1 | A @ 1 |
|  | B @ 5 | A @ 5 |
| 20 | C @ 0.1 | A @ 0.1 |
|  | B @ 1 | A @ 1 |
|  | A @ 5 | A @ 5 |
| 22 | B @ 0.1 | A @ 0.1 |
|  | B @ 1 | A @ 1 |
|  | A @ 5 | A @ 5 |
| 24 | C @ 1 | A @ 1 |
|  | A @ 5 | A @ 5 |

Feces Excretion Time
A: 301-400 min, B: 401-500 min, C: 501-590 min, D: 591-600 min
Percentage of subjects excreting feces within 10 hours (%)
A: 76-100%, B: 50-75%, C: <50%

The reduction in feces excretion time and the increase in percentage of rats excreting feces within 10 hours are closely related to relief from constipation symptoms. As shown in Table 1, the experimental rats administered with the compounds of the present invention excreted feces within a reduced time and also a significantly higher percentage in the number of rats showed excretion of feces within 10 hours, compared to the control rats administered with a methylcellulose vehicle, which is known to prevent constipation by controlling intestinal functions. Additionally, when the administration dose of the compounds of the present invention was lowered to a level from 1/5 to 1/50, the resulting effects were shown to be equal to or better than that of the vehicle administration. This suggests that the compounds of the present invention can effectively prevent or treat constipation.

What is claimed is:
1. A compound represented by Formula 1 below, or a pharmaceutically acceptable salt thereof:

[Formula 1]

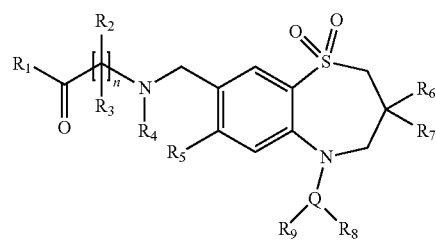

wherein
R₁ is hydroxy, carboxy, or hydroxysulfonyl(C₁₋₄ alkyl);
R₂ and R₃ are each independently hydrogen, C₁₋₄ alkyl, hydroxy (C₁₋₄ alkyl);
carbamoyl(C₁₋₄ alkyl), carboxy, carboxy(C₁₋₄ alkyl), (C₅₋₁₀ heteroaryl)(C₁₋₄ alkyl), or (C₅₋₁₀ aryl)(C₁₋₄ alkyl), or R₂ and R₃, taken together with the respective carbon atom to which they are attached, form C₃₋₇ cycloalkylene;
R₄ is hydrogen or carboxy(C₁₋₄ alkyl);
R₅ is hydrogen, halogen, (C₁₋₄ alkyl)thio, (C₁₋₄ alkyl) amino, or di(C₁₋₄ alkyl)amino;
R₆ and R₇ are each independently C₁₋₆ alkyl;
R₈ and R₉ are each independently hydrogen, hydroxy, C₁₋₄ alkoxy, C₁₋₄ alkyl, halogen, nitro, cyano, amino, (C₁₋₄ alkyl)amino, di(C₁₋₄ alkyl)amino, acetamido, formyl, C₁₋₄ alkanoyl, carboxy, carbamoyl, (C₁₋₄ alkyl)carbamoyl, di(C₁₋₄ alkyl)carbamoyl, carbamoyloxy, (C₁₋₄ alkyl)carbamoyloxy, di(C₁₋₄ alkyl)carbamoyloxy, (C₁₋₄ alkyl)sulfonyloxy, sulfamoyloxy, (C₁₋₄ alkyl)sulfamoyloxy, or di(C₁₋₄ alkyl)sulfamoyloxy;
Q is C₅₋₁₀ aryl or C₅₋₁₀ heteroaryl; and
n is an integer of 0 to 3.

2. The compound of claim 1 or a pharmaceutically acceptable salt thereof, wherein
R₁ is hydroxy, carboxy, or hydroxysulfonyl(C₁₋₄ alkyl);
R₂ and R₃ are each independently hydrogen, C₁₋₄ alkyl, hydroxy(C₁₋₄ alkyl), carbamoyl(C₁₋₄ alkyl), carboxy, carboxy(C₁₋₄ alkyl), or (C₅₋₁₀ heteroaryl)(C₁₋₄ alkyl), or R₂ and R₃, taken together with the respective carbon atom to which they are attached, form C₃₋₇ cycloalkylene;
R₄ is hydrogen or carboxy(C₁₋₄ alkyl);
R₅ is (C₁₋₄ alkyl)thio;
R₆ and R₇ are each independently C₁₋₆ alkyl;
R₈ and R₉ are each independently hydrogen, hydroxy, halogen, or C₁₋₄ alkoxy;
Q is C₅₋₁₀ aryl; and
n is an integer of 0 to 3.

3. The compound of claim 1 or a pharmaceutically acceptable salt thereof, wherein R₁ is hydroxy, carboxy, or hydroxysulfonylmethyl.

4. The compound of claim 1 or a pharmaceutically acceptable salt thereof, wherein R₂ and R₃ are each independently hydrogen, carboxy, methyl, isobutyl, carbamoylmethyl, carboxymethyl, carboxyethyl, hydroxymethyl, imidazolylmethyl, indolylmethyl, or ethyl, or R₂ and R₃, taken together with the respective carbon atom to which they are attached, form cyclopropylene.

5. The compound of claim 1 or a pharmaceutically acceptable salt thereof, wherein R₄ is hydrogen, carboxymethyl, or carboxyethyl.

6. The compound of claim 1 or a pharmaceutically acceptable salt thereof, wherein R₅ is methylthio, ethylthio, or dimethylamino.

7. The compound of claim 1 or a pharmaceutically acceptable salt thereof, wherein R₆ and R₇ are both butyl or both ethyl.

8. The compound of claim 1 or a pharmaceutically acceptable salt thereof, wherein R₈ and R₉ are each independently hydrogen, hydroxy, methoxy, methyl, ethyl, fluoro, chloro, nitro, cyano, amino, methylamino, ethylamino, dimethylamino, acetyl, carboxy, carbamoyl, methylcarbamoyl, dimethylcarbamoyl, carbamoyloxy, methylcarbamoyloxy, dimethylcarbamoyloxy, methylsulfonyloxy, sulfamoyloxy, methylsulfamoyloxy, or dimethylsulfamoyloxy.

9. The compound of claim 1 or a pharmaceutically acceptable salt thereof, wherein Q is phenyl, pyridinyl, pyrimidinyl, or thiophenyl.

10. The compound or a pharmaceutically acceptable salt thereof of claim 1, wherein the compound is selected from the group consisting of:
1) 2-(((3,3-dibutyl-7-methylthio-1,1-dioxido-5-phenyl-2,3,4,5-tetrahydrobenzo[b][1,4]thiazepine-8-yl)methyl)amino)acetic acid;
2) 3-(((3,3-dibutyl-7-methylthio-1,1-dioxido-5-phenyl-2,3,4,5-tetrahydrobenzo[b][1,4]thiazepine-8-yl)methyl)amino)propanoic acid;
3) 2-(((3,3-dibutyl-7-methylthio-1,1-dioxido-5-phenyl-2,3,4,5-tetrahydrobenzo[b][1,4]thiazepine-8-yl)methyl)amino)succinic acid;
4) (S)-2-(((3,3-dibutyl-7-methylthio-1,1-dioxido-5-phenyl-2,3,4,5-tetrahydrobenzo[b][1,4]thiazepine-8-yl)methyl)amino)propanoic acid;
5) 2-(((3,3-dibutyl-7-methylthio-1,1-dioxido-5-phenyl-2,3,4,5-tetrahydrobenzo[b][1,4]thiazepine-8-yl)methyl)amino)pentanedioic acid;
6) 4-amino-2-(((3,3-dibutyl-7-methylthio-1,1-dioxido-5-phenyl-2,3,4,5-tetrahydrobenzo[b][1,4]thiazepine-8-yl)methyl)amino)-4-oxobutanoic acid;
7) (R)-2-(((3,3-dibutyl-7-methylthio-1,1-dioxido-5-phenyl-2,3,4,5-tetrahydrobenzo[b][1,4]thiazepine-8-yl)methyl)amino)propanoic acid;
8) 2-(((3,3-dibutyl-7-methylthio-1,1-dioxido-5-phenyl-2,3,4,5-tetrahydrobenzo[b][1,4]thiazepine-8-yl)methyl)amino)-2-methylpropanoic acid;
9) (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-imidazol-4-yl)propanoic acid;
10) (R)-2-(((3,3-dibutyl-7-methylthio-1,1-dioxido-5-phenyl-2,3,4,5-tetrahydrobenzo[b][1,4]thiazepine-8-yl)methyl)amino)-3-(1H-indol-2-yl)propanoic acid;
11) (S)-2-(((3,3-dibutyl-7-methylthio-1,1-dioxido-5-phenyl-2,3,4,5-tetrahydrobenzo[b][1,4]thiazepine-8-yl)methyl)amino)-4-methylpentanoic acid;
12) (S)-2-(((3,3-dibutyl-7-methylthio-1,1-dioxido-5-phenyl-2,3,4,5-tetrahydrobenzo[b][1,4]thiazepine-8-yl)methyl)amino)pentanedioic acid;
13) (S)-2-(((3,3-dibutyl-7-methylthio-1,1-dioxido-5-phenyl-2,3,4,5-tetrahydrobenzo[b][1,4]thiazepine-8-yl)methyl)amino)-3-hydroxypropanoic acid;
14) 3-((carboxymethyl)((3,3-dibutyl-7-methylthio-1,1-dioxido-5-phenyl-2,3,4,5-tetrahydrobenzo[b][1,4]thiazepine-8-yl)methyl)amino)propanoic acid;
15) 3-(((3,3-dibutyl-7-methylthio-1,1-dioxido-5-phenyl-2,3,4,5-tetrahydrobenzo[b][1,4]thiazepine-8-yl)methyl)amino)pentanedioic acid;
16) 2-(((3,3-dibutyl-7-methylthio-1,1-dioxido-5-phenyl-2,3,4,5-tetrahydrobenzo[b][1,4]thiazepine-8-yl)methyl)amino)-2-oxoacetic acid;
17) 1-(((3,3-dibutyl-7-methylthio-1,1-dioxido-5-phenyl-2,3,4,5-tetrahydrobenzo[b][1,4]thiazepine-8-yl)methyl)amino)cyclopropanecarboxylic acid;
18) 2-(((3,3-dibutyl-7-methylthio-1,1-dioxido-5-phenyl-2,3,4,5-tetrahydrobenzo[b][1,4]thiazepine-8-yl)methyl)amino)-2-oxoethanesulfonic acid;
19) 2-4(3,3-dibutyl-5-(4-methoxyphenyl)-7-methylthio-1,1-dioxido-2,3,4,5-tetrahydrobenzo[b][1,4]thiazepine-8-yl)methyl)amino)acetic acid;
20) 2-(((3,3-dibutyl-5-(4-hydroxyphenyl)-7-methylthio-1,1-dioxido-2,3,4,5-tetrahydrobenzo[b][1,4]thiazepine-8-yl)methyl)amino)acetic acid;

21) 2-(((3,3-dibutyl-5-(3-methoxyphenyl)-7-methylthio-1,1-dioxido-2,3,4,5-tetrahydrobenzo[b][1,4]thiazepine-8-yl)methyl)amino)acetic acid;
22) 2-(((3,3-dibutyl-5-(4-fluorophenyl)-7-methylthio-1,1-dioxido-2,3,4,5-tetrahydrobenzo[b][1,4]thiazepine-8-yl)methyl)amino)acetic acid;
23) 2-(((3,3-dibutyl-5-(3-fluorophenyl)-7-methylthio-1,1-dioxido-2,3,4,5-tetrahydrobenzo[b][1,4]thiazepine-8-yl)methyl)amino)acetic acid;
24) 2-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)acetic acid;
25) 2-(((3,3-dibutyl-5-(4-methoxyphenyl)-7-methylthio-1,1-dioxido-2,3,4,5-tetrahydrobenzo[b][1,4]thiazepine-8-yl)methyl)amino)-2-oxoethanesulfonic acid;
26) 1-(((3,3-dibutyl-5-(3-fluoro-4-methoxyphenyl)-7-methylthio-1,1-dioxido-2,3,4,5-tetrahydrobenzo[b][1,4]thiazepine-8-yl)methyl)amino)cyclopropanecarboxylic acid;
27) 2-(((3,3-dibutyl-5-(4-fluorophenyl)-7-methylthio-1,1-dioxido-2,3,4,5-tetrahydrobenzo[b][1,4]thiazepine-8-yl)methyl)amino)-2-oxoacetic acid;
28) (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)propanoic acid;
29) (S)-2-(((3,3-dibutyl-5-(4-fluorophenyl)-7-methylthio-1,1-dioxido-2,3,4,5-tetrahydrobenzo[b][1,4]thiazepine-8-yl)methyl)amino)-3-hydroxypropanoic acid; and
30) 1-(((3,3-dibutyl-5-(4-fluorophenyl)-7-methylthio-1,1-dioxido-2,3,4,5-tetrahydrobenzo[b][1,4]thiazepine-8-yl)methyl)amino)cyclopropanecarboxylic acid.

11. A pharmaceutical composition comprising the compound according to claim 1 or a pharmaceutically acceptable salt thereof.

12. A pharmaceutical composition comprising the compound according to claim 10 or a pharmaceutically acceptable salt thereof.

13. A method for treating constipation in a subject in need thereof, the method comprising administering an effective amount of the compound according to claim 1 or a pharmaceutically acceptable salt thereof to the subject, thereby treating constipation.

14. A method for treating constipation in a subject in need thereof, the method comprising administering an effective amount of the compound according to claim 10 or a pharmaceutically acceptable salt thereof to the subject, thereby treating constipation.

* * * * *